United States Patent [19]

Jacobellis

[11] 4,344,439

[45] Aug. 17, 1982

[54] CATHETER FOR USE IN LOCALIZING THE ORIGIN OF IDIOPATHIC MICROSCOPIC HEMATURIA

[76] Inventor: Ulrico Jacobellis, Via Andrea Da Bari 128, 70121 Bari, Italy

[21] Appl. No.: 198,711

[22] Filed: Oct. 20, 1980

[51] Int. Cl.³ .................. A61M 25/00; A61B 10/00
[52] U.S. Cl. ................. 128/636; 128/349 R; 128/771
[58] Field of Search .............. 128/632, 636, 638, 768, 128/771, 349 R, 757, 759

[56] References Cited

U.S. PATENT DOCUMENTS

| | | | |
|---|---|---|---|
| 617,016 | 1/1899 | Harris | 128/349 R |
| 3,037,496 | 6/1962 | Melges | 128/636 |
| 3,373,735 | 3/1968 | Gallagher | 128/768 |
| 3,627,698 | 12/1971 | Rey et al. | 23/913 |
| 3,672,351 | 6/1972 | Ubersax et al. | 128/638 |
| 3,943,929 | 3/1976 | Patel | 128/349 R X |
| 4,168,699 | 9/1979 | Hauser | 128/768 |

Primary Examiner—Dalton L. Truluck
Attorney, Agent, or Firm—John Cyril Malloy

[57] ABSTRACT

A ureteral catheter comprising a tip of reactive reagent material to detect the presence of blood or hemoglobin in the urine from one of the ureters or kidney at the mouth of the ureters into the bladder and which catheter is sized for insertion through a cystoscope.

4 Claims, 2 Drawing Figures

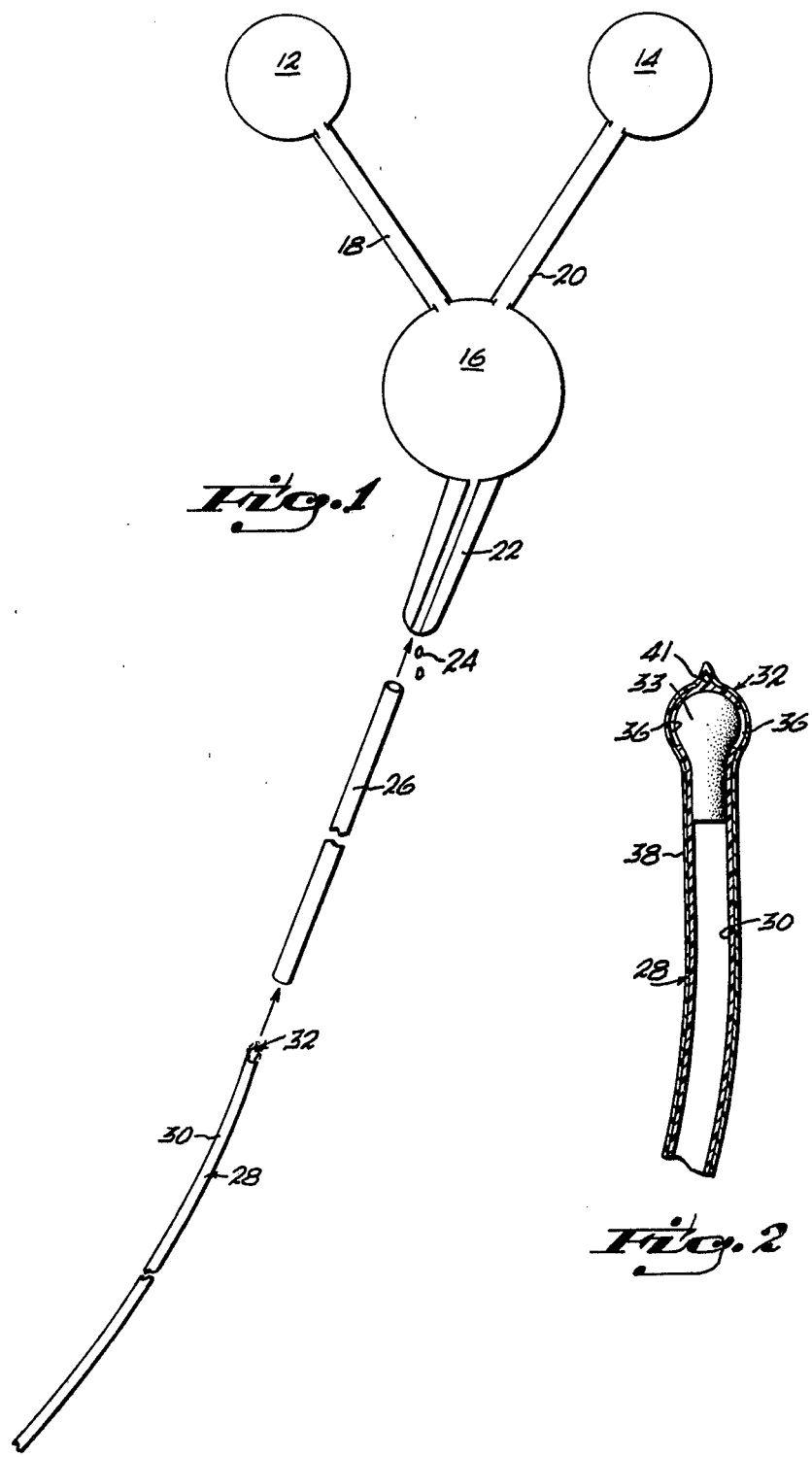

CATHETER FOR USE IN LOCALIZING THE ORIGIN OF IDIOPATHIC MICROSCOPIC HEMATURIA

BACKGROUND OF THE INVENTION

Essential or so-called idiopathic microscopic hematuria remains an unsolved problem for urologists and nephrologists, despite improvements in diagnostic methods. The problem, quite often, is that a patient is determined to have some blood cells in his urine. When this occurs, especially if they are small in number, it is difficult to know whether the same originate in the upper or the lower urinary tract. For this reason, sometimes a patient although he has blood in the urine in small quantities is told to return after a set period of time for further checking. With this invention it is possible to determine the area of the urinary tract affected which is an important first step in making a diagnosis. It is a purpose, therefore, of this invention to provide a catheter which is useful in making such a diagnosis.

GENERAL DESCRIPTION OF THE OPERATION OF THE INVENTION

This invention is useful to discriminate between upper tract and lower tract microscopic hematuria. Moreover, it will determine, if it is from the upper tract, whether the hematuria is from the left or right kidney. In use, after water cystoscopy, an air cystoscopy is performed. The distilled water reservoir is connected to a bottle containing air with a two channel plug. As the distilled water flows down into the bottle, air passes out into the cystoscope sheath and into the bladder. Air prevents the reactive strip from becoming damp. Once the bladder is partially inflated with air, and both ureteral meatus are clearly visualized, a hemostick is introduced using the catheter through the operating cystoscope. The end of the catheter which is of a reactive reagent material is placed close to the ureteral meatus and one or two drops of urine will eventually impregnate the material. The material is then withdrawn using the catheter and a plastic sheath is utilized to avoid dampening it during this procedure. A ureteral catheter is utilized to drain the urine from the bladder throughout the test preferably.

If the microscopic hematuria comes from the kidney being tested, the strip changes color from yellow to green. Its color is compared with the double chromatic scale standard, with one scale for homoglobin and one for erythrocytes. The same procedure is performed with the other ureteral meatus. If the impregnated strips do not change color, then the microscopic hematuria does not originate in the kidneys or ureters, but comes from the lower urinary tract, that is the bladder, urethra and other associated organs. The prescence of microscopic hematuria must be confirmed on the same day as the test. One hour before the test, the patient must drink several glasses of water to increase diuresis. In some cases, the test is repeated to confirm the result.

OBJECTS OF THIS INVENTION

It is an object, therefore, of this invention to provide an improved catheter for localizing the origin of idiopathic microscopic hematuria.

It is a further object of this invention to provide the new and simple technique to distinguish which area of the urinary tract is affected by idiopathic microscopic hematuria. The catheter is composed of a tip to be introduced in the bladder through an operating cystoscope and placed close to the ureteral meatus during air cystoscopy. Air prevents the reactive strip from becoming damp and the strip is moistened only with urine.

It is another object of this invention to provide a catheter which is simple to use, not traumatic to the patient, and does not require hospitalization of the patient, involves little risk and danger, and can be provided at minimal cost with no special equipment being required.

In accordance with these and other objects which will become apparent hereinafter the instant invention will now be described with reference to the accompanying drawings in which:

DESCRIPTION OF THE DRAWINGS

FIG. 1 is an exploded schematic view of the catheter of the present invention in use; and FIG. 2 is an enlarged sectional view of the leading tip end of the catheter.

DESCRIPTION OF THE PREFERRED EMBODIMENT

Referring to the drawings wherein like reference characters designate like or corresponding parts throughout the several views there is shown, schematically, a kidney 12 and kidney 14 which are joined to a bladder 16 of a person by means of urether 18 and 20 respectively. The bladder through the lower urinary exhausts system 22 exhausts the urine from the kidney as is indicated by the numeral 24. Oftentimes blood cells will be found in the urine; however, it will not be known whether it comes from the upper part of the system, that is from the kidneys or urethers. This invention employs a standard commercially available cystoscope generally designated by the numeral 26 which includes a tube. It is composed of a catheter generally indicated by the numeral 28 now to be described. The catheter it is seen is composed of a plastic tube 30 with a tip 32 which is composed of a reactive reagent material to detect the presence of blood and hemoglobin in the urine and which is commercially available and which is in the form of a wad and designated by the numeral 33. Preferably it is within a bulbous tip which has a plurality of openings such as 36. Preferably about the tip and catheter there is provided a thin film sheath easily pierceable such as that designated by the numeral 38. In use, the catheter 28 is inserted through the cystoscope 26 into the bladder and at the zone of juncture of mouth of one of the urethers leading into the bladder. The sheath is utilized to keep the reagent material dry. When a droplet or so of urine is about to enter the bladder, it will be absorbed by the reagent material causing it to change color. In order to expose it, the tube, carrying the reagent material is forced through the plastic material and to this end preferably the end has a tip 41. The reagent material will change color and, by this means a test may be performed to determine whether or not blood cells in urine are coming from the upper portion of the urinary system and, if so, from which of the kidneys and associated urethra.

It is thus seen that there has been provided a simple and inexpensive device for the purpose of determining if blood cells come from the upper portion of the system and, if so, from which kidney and urethra.

What is claimed is:

1. For use with a conventional cystoscope a ureteral catheter comprising an elongated tubular member having an insertion tip, said tip having opening means therein and including means therein for detecting the presence of blood or hemoglobin in the urine from one of the ureters or kidney at the mouth of the ureters into the bladder upon insertion of the tip into the bladder, said catheter being sized for coaxial insertion through the cystoscope said detecting means comprising a color reactive agent material mounted adjacent said opening means within said tip.

2. The device as set forth in claim 1 wherein the catheter is composed of plastic.

3. The device as set forth in claim 1 wherein said tube tip is composed of an open work plastic structure and said reagent material comprises a wad means captivated within said open work plastic structure.

4. The device as set forth in claim 1 wherein a protective film jacket is provided on said tube and in covering relation of said tip, said film being pierceable by movement of said tube and tip axially with respect to said film to maintain said reagent material normally in a dry film protective condition during insertion.

* * * * *